US006926660B2

(12) United States Patent
Miller

(10) Patent No.: US 6,926,660 B2
(45) Date of Patent: Aug. 9, 2005

(54) FACILITATING TREATMENT VIA MAGNETIC STIMULATION

(75) Inventor: Stanford W. Miller, Kennesaw, GA (US)

(73) Assignee: Neuronetics, Inc.

(*) Notice: Subject to any disclaimer, the term of this patent is extended or adjusted under 35 U.S.C. 154(b) by 0 days.

(21) Appl. No.: 10/794,110

(22) Filed: Mar. 5, 2004

(65) Prior Publication Data

US 2004/0193001 A1 Sep. 30, 2004

Related U.S. Application Data

(60) Provisional application No. 60/452,477, filed on Mar. 7, 2003.

(51) Int. Cl.[7] ................................................. A61N 2/00
(52) U.S. Cl. .......................................... 600/9; 606/130
(58) Field of Search ....................... 600/9–15, 382–383; 606/130

(56) References Cited

U.S. PATENT DOCUMENTS

| 3,683,923 A | 8/1972 | Anderson | 128/303.14 |
| 4,712,558 A | 12/1987 | Kidd et al. | 128/421 |
| 4,994,015 A | 2/1991 | Cadwell | 600/13 |
| 4,995,395 A | 2/1991 | Ilmoniemi et al. | 128/653 |

(Continued)

FOREIGN PATENT DOCUMENTS

| EP | 1 273 320 A1 | 1/2003 |
| WO | WO 99/64884 | 12/1999 |
| WO | WO 00/74777 | 12/2000 |
| WO | WO 01/12236 A2 | 2/2001 |
| WO | WO 01/28622 A2 | 4/2001 |
| WO | WO 01/97906 A2 | 12/2001 |
| WO | WO 02/09811 A1 | 2/2002 |
| WO | WO 02/31604 A1 | 4/2002 |
| WO | WO 02/032504 A2 | 4/2002 |
| WO | WO 02/072194 A2 | 9/2002 |
| WO | WO 02/085449 A2 | 10/2002 |
| WO | WO 02/085454 A1 | 10/2002 |
| WO | WO 02/089902 A2 | 11/2002 |
| WO | WO 02/094997 A2 | 11/2002 |
| WO | WO 03/035163 A2 | 5/2003 |
| WO | WO 03/039468 A2 | 5/2003 |
| WO | WO 03/082405 A1 | 10/2003 |
| WO | WO 03/084605 A1 | 10/2003 |
| WO | WO 03/085546 A1 | 10/2003 |
| WO | WO 03/090604 A2 | 11/2003 |
| WO | WO 03/098268 A1 | 11/2003 |
| WO | WO 2004/006750 A2 | 1/2004 |
| WO | WO 2004/082759 A2 | 9/2004 |

OTHER PUBLICATIONS

Baudewig, J. et al., "Functional MRI of Cortical Activations Induced by Transcranial Magnetic Stimulation(TMS)", *Brain Imaging–NeuroReport*, 2001, 12(16), 3543–3548.

(Continued)

*Primary Examiner*—John P. Lacyk
(74) *Attorney, Agent, or Firm*—Woodcock Washburn LLP

(57) ABSTRACT

The invention provides a device, system and method for placing a treatment component on a patient's head. The inventive device includes an attachment frame that attaches the treatment component to the patient's head. The attachment frame also includes a window. A receiving mechanism holds the treatment component to the attachment frame, and an alignment structure permits the treatment component to be positioned at a desired location on the patient's head. The inventive device also may include an isolator component capable of reducing sound to the patient's ears and/or reducing vibration of the attachment frame. The inventive may also include an electrical connector to send and receive data based on the treatment, and an adjustment structure that is capable of adjusting the device to each patient.

26 Claims, 2 Drawing Sheets

U.S. PATENT DOCUMENTS

| | | | |
|---|---|---|---|
| 5,078,674 A | 1/1992 | Cadwell | 600/13 |
| 5,097,833 A | 3/1992 | Campos | 607/68 |
| 5,116,304 A | 5/1992 | Cadwell | 600/13 |
| 5,154,723 A * | 10/1992 | Kubota et al. | 606/130 |
| 5,566,681 A * | 10/1996 | Manwaring et al. | 5/622 |
| 5,707,334 A | 1/1998 | Young | 600/9 |
| 5,769,778 A | 6/1998 | Abrams et al. | 600/14 |
| 5,813,970 A | 9/1998 | Abrams et al. | 600/14 |
| 6,057,373 A | 5/2000 | Fogel | 514/740 |
| 6,066,084 A | 5/2000 | Edrich et al. | 600/13 |
| 6,117,066 A | 9/2000 | Abrams et al. | 600/14 |
| 6,155,966 A | 12/2000 | Parker | 600/13 |
| 6,169,963 B1 | 1/2001 | Markov | 702/57 |
| 6,179,769 B1 | 1/2001 | Ishikawa et al. | 600/9 |
| 6,179,771 B1 | 1/2001 | Mueller | 600/13 |
| 6,198,958 B1 | 3/2001 | Ives et al. | 600/411 |
| 6,253,109 B1 | 6/2001 | Gielen | 607/45 |
| 6,256,531 B1 | 7/2001 | Ilmoniemi et al. | 600/544 |
| 6,366,814 B1 | 4/2002 | Boveja et al. | 607/45 |
| 6,389,318 B1 | 5/2002 | Zarinetchi et al. | 607/61 |
| 6,402,678 B1 | 6/2002 | Fischell et al. | 600/13 |
| 6,463,328 B1 | 10/2002 | John | 607/45 |
| 6,484,059 B2 | 11/2002 | Gielen | 607/45 |
| 6,488,617 B1 | 12/2002 | Katz | 600/26 |
| 6,497,648 B1 | 12/2002 | Rey | 600/14 |
| 6,503,187 B1 | 1/2003 | Ilmoniemi et al. | 600/14 |
| 6,516,288 B2 | 2/2003 | Bagne | 702/179 |
| 6,537,197 B1 | 3/2003 | Ruohonen et al. | 600/13 |
| 6,551,233 B2 | 4/2003 | Perreault et al. | 600/9 |
| 6,560,490 B2 | 5/2003 | Grill et al. | 607/72 |
| 6,567,702 B1 | 5/2003 | Nekhendzy et al. | 607/46 |
| 6,571,123 B2 | 5/2003 | Ives et al. | 600/544 |
| 6,572,528 B2 | 6/2003 | Rohan et al. | 600/14 |
| 6,618,614 B1 * | 9/2003 | Chance | 600/473 |
| 6,629,935 B1 | 10/2003 | Miller et al. | 600/558 |
| 6,663,556 B2 | 12/2003 | Barker | 600/14 |
| 2001/0031906 A1 | 10/2001 | Ishikawa et al. | 600/13 |
| 2002/0013612 A1 | 1/2002 | Whitehurst | 607/45 |
| 2002/0087201 A1 | 7/2002 | Firlik et al. | 607/45 |
| 2002/0091419 A1 | 7/2002 | Firlik et al. | 607/45 |
| 2002/0103515 A1 | 8/2002 | Davey et al. | 607/66 |
| 2002/0123780 A1 | 9/2002 | Grill et al. | 607/72 |
| 2002/0160436 A1 | 10/2002 | Markov et al. | 435/15 |
| 2002/0169355 A1 | 11/2002 | Rohan et al. | 600/9 |
| 2003/0004392 A1 | 1/2003 | Tanner et al. | 600/9 |
| 2003/0023159 A1 | 1/2003 | Tanner | 600/417 |
| 2003/0028072 A1 | 2/2003 | Fischell et al. | 600/13 |
| 2003/0050527 A1 | 3/2003 | Fox et al. | 600/13 |
| 2003/0073899 A1 | 4/2003 | Ruohonen et al. | 600/417 |
| 2003/0074032 A1 | 4/2003 | Gliner et al. | 607/45 |
| 2003/0082507 A1 | 5/2003 | Stypulkowski | 434/262 |
| 2003/0087264 A1 | 5/2003 | Kaplitt et al. | 435/6 |
| 2003/0088274 A1 | 5/2003 | Gliner et al. | 607/3 |
| 2003/0097161 A1 | 5/2003 | Firlik et al. | 607/72 |
| 2003/0125786 A1 | 7/2003 | Gliner et al. | 607/116 |
| 2003/0130706 A1 | 7/2003 | Sheffield et al. | 607/46 |
| 2003/0195588 A1 | 10/2003 | Fischell et al. | 670/55 |
| 2003/0204135 A1 | 10/2003 | Bystritsky | 600/407 |
| 2004/0010177 A1 | 1/2004 | Rohan et al. | 600/9 |
| 2004/0138550 A1 | 7/2004 | Hartlep et al. | 600/407 |
| 2004/0143300 A1 | 7/2004 | Rogers | 607/45 |

OTHER PUBLICATIONS

Bohning, D.E. et al., "A TMS Coil Positioning/Holding System for MR Image–Guided TMS Interleaved with fMRI", *Clinical Neurophysiology,* 2003, 114, 2210–2219.

Bohning, D.E. Ph.D. et al., "A Combined TMS/fMRI Study of Intensity–Dependant TMS over Motor Cortex", *Society of Biological Psychiatry,* 1999, 45, 385–394.

Bohning, D.E. Ph.D. et al., "BOLD–fMRI Response to Single–Pulse Transcranial Magnetic Stimulation (TMS)", *Journal of Magnetic Resonance Imaging,* 2000, 11, 569–574.

Garcia–Toro, M. et al., "Modest Adjunctive Benefit with Transcranial Magnetic Stimulation in Medication–Resistant Depression", *Journal of Affective Disorders,* 2001, 64, 271–275.

George, M.S. et al., "A Controlled Trial of Daily Left Prefrontal Cortex TMS for Treating Depression", *Society of Biological Psychiatry,* 2000, 48, 962–970.

George, M.S. "New Methods of Minimally Invasive Brain Modulation as Therapies in Psychiatry: TMS,MST,VNS and DBS", *Chinese Medical Journal (Taipei),* 2002, 65, 349–360.

Grafman, J. Ph.D., "TMS as a Primary Brain Mapping Tool" *Transcranial Magnetic Stimulation in Neuropsychiatry,* 2000, 115–140.

Nahas, Z.et al., "Left Prefrontal Transcranial Magnetic Stimulation(TMS) Treatment of Depression in Bipolar Affective Disorder: A Pilot Study of Acute Safety and Efficacy", *Bipolar Disorders,* 2003, 5, 40–47.

Lisanby, S.H. MD. et al., "Magnetic Seizure Therapy of Major Depression", *Arch Gen Psychiatry,* 2001, 58, 303–307.

Lisanby, S.H. et al., "Sham TMS: Intracerebral Measurement of the Induced Electrical Field and the Induction of Motor–Evoked Potentials", *Society of Biological Psychiatry,* 2001, 49, 460–463.

Lisanby, S.H., "Safety and Feasibility of Magnetic Seizure Therapy(MST) in Major Depression: Randomized Within–Subject Comparasion with Electroconvulsive Therapy", *Neuropsychopharmacology, New York State Psychiatric Institute,* 2003, 28, 1852–1865.

Lisanby, S.H., "Update on Magnetic Seizure Therapy: A Novel Form of Convulsive Therapy", *The Journal of ECT,* 2002, 18, 182–188.

Lorberbaum, J.P., M.D. et al., "Safety Concerns of TMS", *Transcranial Magnetic Stimulation in Neuropsychiatry,* 2000, 141–161.

Loo, C.K. et al., "Transcranial Magnetic Stimulation (TMS) in Controlled Treatment Studies: Are Some "Sham" Forms Active?", *Society of Biological Psychiatry,* 2000, 47, 325–331.

Nahas, Z. et al., "Unilateral Left Prefrontal Transcranial Magnetic Stimulation(TMS) Produces Intensity–Dependent Bilateral Effects as Measured by Interleaved BOLD fMRI", *Society of Biological Psychiatry,* 2001, 50, 712–720.

Pridmore, S., "Substitution of Rapid Transcranial Magnetic Stimulation Treatments for Electroconvulsive Therapy Treatments in a Course of Electroconvulsive Therapy", *depression and Anxiety,* 2000, 12, 118–123.

Roth, Y. et al., "A Coil Design for Transcranial Magnetic Stimulation of Deep Brain Regions", *Journal of Clinical Neurophysiology,* 2002, 19(4), 361–370.

Ruohonen, J., "Electroencephalography Combined with TMS", BioMag Laboratory, Helsinki University Central Hospital, http://www.biomag.helsinki.fi/tms/TMSEE-G.html, Oct. 6, 1999, 22 pages.

Terrace, H.S. et al., "The Cognitive Effects of Electroconvulsive Shock and Magnetic Seizure Therapy in Rhesus Monkeys", *Society for Neuroscience Abstract Viewer and Itinerary Planner*, 2002, Abstract Only # 184.14.

Terrace, H.S. et al., "The Cognitive Effects of Electroconvulsive Shock Stimulation and Magnetic Seizure Therapy in Rhesus Monkeys", *Society for Neuroscience Abstracts*, 2001, 27(1), 536.7, p. 1418.

Trivedi, M.H., MD., "Treatment–Resistant Depression: New Therapies on the Horizon", *Annals of Clinical Psychiatry*, 2003, 15(1), 59–70.

* cited by examiner

FACILITATING TREATMENT VIA MAGNETIC STIMULATION

CROSS-REFERENCE TO RELATED APPLICATION

This application claims priority under 35 U.S.C. § 119 (e) to U.S. provisional application Ser. No. 60/452,477, filed on Mar. 7, 2003, entitled "Device, Method, and System for the Reduction of Discomfort Associated with and Facilitating Treatment via Magnetic Stimulation," which is herein incorporated by reference in its entirety. This application is related to co-pending U.S. patent application Ser. No. 10/657,296 filed Sep. 8, 2003 entitled "Reducing Discomfort Caused by Electrical Stimulation;" U.S. patent application Ser. No. 10/672,833 filed Sep. 26, 2003 entitled "Reducing Discomfort Caused by Electrical Stimulation;" U.S. patent application Ser. No. 10/729,243 filed Dec. 5, 2003 entitled "Reducing Discomfort Caused by Electrical Stimulation;" and U.S. patent application Ser. No. 10/792,994 filed Mar. 4, 2004 entitled "Reducing Discomfort Caused by Electrical Stimulation;" all of which are herein incorporated by reference in their entirety.

FIELD OF THE INVENTION

The invention relates to the field of magnetic stimulation. More specifically, the invention relates to facilitating the administration of transcutaneous magnetic stimulation.

BACKGROUND OF THE INVENTION

A number of medical ailments are treated or treatable through the application of a magnetic field to an afflicted portion of a patient's body. Neurons and muscle cells are a form of biological circuitry that carry electrical signals and respond to electromagnetic stimuli. When an ordinary conductive wire is passed through a magnetic field, an electric current is induced in the wire. The same principle holds true for biological tissue. When a strong magnetic field is applied to a portion of the body, neurons are depolarized and stimulated. Muscles associated with the stimulated neurons contract as though the neurons were firing normally.

The use of magnetic stimulation is thus very effective in rehabilitating injured or paralyzed muscle groups. Further, the process is non-invasive, since magnetic fields easily pass through the skin of a patient. Apart from stimulation of large muscle groups such as the thigh or the abdomen, experimentation has been performed in cardiac stimulation as well. In this context, magnetic stimulation of the heart may prove to be superior to CPR or electrical stimulation, because both of those methods apply gross stimulation to the entire heart all at once. A magnetic stimulator can be used as an external pacer to stimulate each chamber of the heart separately in the proper sequence. Another area in which magnetic stimulation is proving effective is treatment of the spine. The spinal cord is difficult to access directly because vertebrae surround it. Magnetic stimulation may be used to block the transmission of pain via nerves in the back, e.g., those responsible for lower back pain.

Magnetic stimulation also has proven effective in stimulating regions of the brain, which is composed predominantly of neurological tissue. One area of particular interest is the treatment of depression. It is believed that more than 28 million Americans suffer from some type of neuropsychiatric disorder. These include conditions such as depression, schizophrenia, mania, obsessive-compulsive disorder, panic disorders, and others. Depression is the "common cold" of psychiatric disorders, believed to affect 19 million Americans and possibly 340 million people worldwide. Modern medicine offers depression patients a number of treatment options, including several classes of anti-depressant medications (Sari's, MAI's and tricyclics), lithium, and electroconvulsive therapy (ECT). Yet many patients remain without satisfactory relief from the symptoms of depression. To date, ECT remains the "gold standard" for depression; however, many patients will not undergo the procedure because of its severe side effects.

Recently, repetitive transcranial magnetic stimulation (rTMS) has been shown to have significant anti-depressant effects for patients that do not respond to the traditional methods. The principle behind rTMS is to apply a subconvulsive stimulation to the prefrontal cortex in a repetitive manner, causing a depolarization of cortical neuron membranes. The membranes are depolarized by the induction of small electric fields in excess of 1 V/cm that are the result of a rapidly changing magnetic field applied non-invasively.

It is now well established that both the left and right prefrontal cortex regions of the brain have strong communication links to Limbic System structures, which contain the "circuits" controlling mood and general behavior. The objective of rTMS is to provide stimulation to these circuits through a non-invasive, sub-convulsive technique, relieving the symptoms of depression without many of the negative side effects of ECT or medications. The principal reported side effect of rTMS is discomfort at the site of stimulation. This is caused by the depolarization of neuron membranes in the scalp and resulting scalp muscle contractions, which occur at the frequency of said stimulation. About 25% of patients report this problem to be at a level that is very uncomfortable. In general, the higher the power and the higher the frequency of stimulation, the more discomfort is reported. Higher power, however, has been shown to be necessary to stimulate deeper midbrain structures directly. High frequencies, (e.g. greater than 1 Hertz) have been shown to have an anti-depressant effect.

A considerable amount of study has been devoted to rTMS, yet the problem of scalp discomfort remains unexamined. For example, U.S. Pat. Nos. 6,198,958 and 6,571,123 are directed to methods of monitoring a patient's brain function during TMS. These references discloses a method for recording an EEG during TMS and for monitoring an MRI scan during TMS. The references also discuss the eddy currents induced in the metal electrodes by the TMS pulses which can cause burning of the patient's scalp by heating of the metal electrodes.

Another area for potential discomfort involved in magnetic stimulation (e.g. rTMS) concerns accurate placement of the coil on the proper location of a patient's head in a quick, easy, and repeatable fashion. The first time a patient receives rTMS treatment, the patient is subjected to a dosing and testing procedure to determine how strong a field is required and permissible and precisely where on the patient's head a physician and/or technician must locate the stimulator coil. Subsequently, it is desired to avoid blindly hunting for the same correct location, so a mark is made on the patient's head. Typically, the patient is provided with a swimming cap that is written on to indicate the correct location of the stimulator coil. However, from treatment to next treatment, the patient may not put the swimming cap on his head in precisely the same location or configuration. Another option practitioners have used is to mark the patient's head directly with a pen. Because this may require shaving the person's head in part or entirely, the patient may feel unhappy with this procedure.

SUMMARY OF THE PREFERRED EMBODIMENTS

The invention provides a device, system and method for placing a treatment component on a patient's head. The inventive device includes an attachment frame that attaches the treatment component to the patient's head. The attachment frame also includes a window. A receiving mechanism holds the treatment component to the attachment frame, and an alignment structure permits the treatment component to be positioned at a desired location on the patient's head. The inventive device also may include an isolator component capable of reducing sound to the patient's ears and/or reducing vibration of the attachment frame. The inventive device may also include an electrical connector to send and receive data based on the treatment, and an adjustment structure that is capable of adjusting the device to each patient. The adjustment structure may be made of a malleable material that helps mold the device to the contours of the patient's head. Also, the malleable material may be made to harden by using a predetermined wavelength of light, heat, and/or an ultrasonic signal. The alignment structure permits the treatment component to be placed in substantially the same location for each patient treatment, and may spans the patient's nose. The inventive device also may include a securing structure including a nose bridge component, a chin strap component, and/or a rear strap component. In addition, the attachment frame may be constructed such that it is reusable or rendered unusable at the conclusion of each patient treatment by modifying the attachment frame, the electrical connector, the alignment structure, receiving mechanism, and/or the malleable material, for example.

The inventive system includes a treatment component, a head-frame component, a flexible circuit capable of being attached to the head-frame component, and an electrical connector in communication with the flexible circuit that communicates data as a function of the treatment component. The head-frame component facilitates placing the treatment component on a patient's head. The flexible circuit may includes a magnetic field sensor to measure the magnetic field being provided to the patient. The treatment component may be, for example, a magnetic stimulation device used for transcutaneous magnetic stimulation treatment of the patient. In this case, the magnetic stimulation device may include an arc-shaped core spanning an angle of less than three hundred sixty degrees, where the core includes a highly saturable magnetic material having a magnetic saturation of at least 0.5 Tesla.

In addition, the invention contemplates a novel method of placing a treatment device on a patient that includes placing a head-frame component on the patient's head, aligning the head-frame component to the patient's head, securing the head-frame component to the patient, and attaching a treatment device to the head-frame component. The inventive method also may include connecting the head-frame component to a computing device. The method also contemplates adjusting the head-frame device to the patient, for example, by causing a malleable portion of the adjustment structure to mold to the patient's head. Such hardening of the malleable portion may be accomplished with the use of a predetermined wavelength of light, heat, and/or an ultrasonic signal, for example.

The invention further includes a system for insuring that the device of the invention is properly placed. Should the wafer circuit be misaligned, the e-fields may not entirely cancel. In the preferred rTMS embodiment, a frame is provided that is repeatedly securable to the head of an rTMS patient that allows for the consistent placement of the magnetic stimulator coil or core and the wafer in the same exact location on the patient's head.

The treatment frame may be provided with a memory circuit for receiving and storing the identity and dosing/treatment information of a given patient.

A wafer circuit may or may not further include a specially designed wire loop to detect the presence of a time varying magnetic field so that the field generated by the rTMS device can be monitored. Additionally, the wafer circuit may or may not also include a specially designed location system, optical or otherwise, to insure correct alignment of the opposing electric field.

DETAILED DESCRIPTION OF THE PREFERRED EMBODIMENTS

Description will now be given with reference to the attached FIGS. 1 and 2. It should be understood that these drawings are exemplary in nature and in no way serve to limit the scope of the invention.

Figure 1:
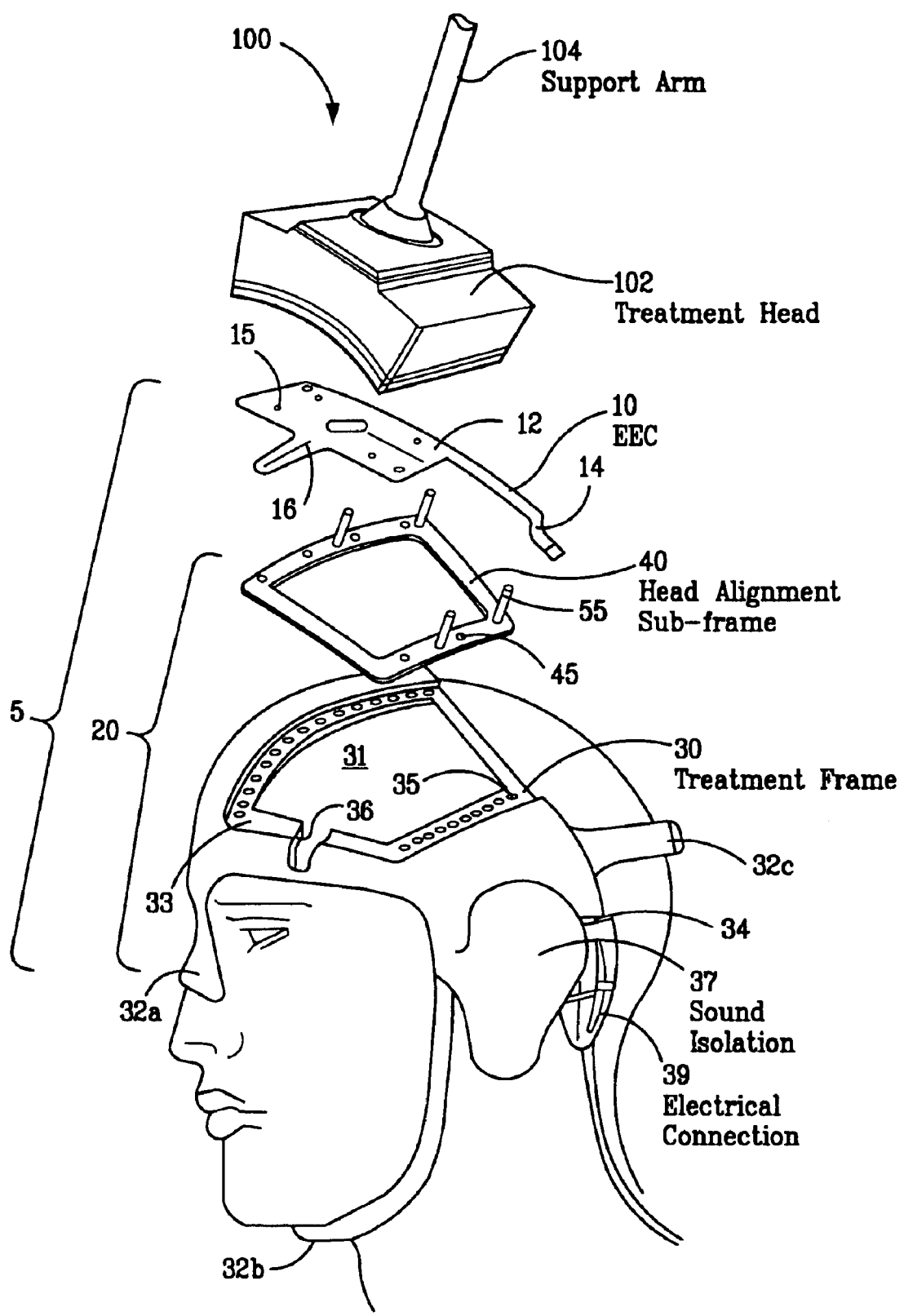
FIG. 1 is an exploded perspective view of a device for reducing scalp nerve membrane depolarization during rTMS in accordance with the invention.
Figure 2:
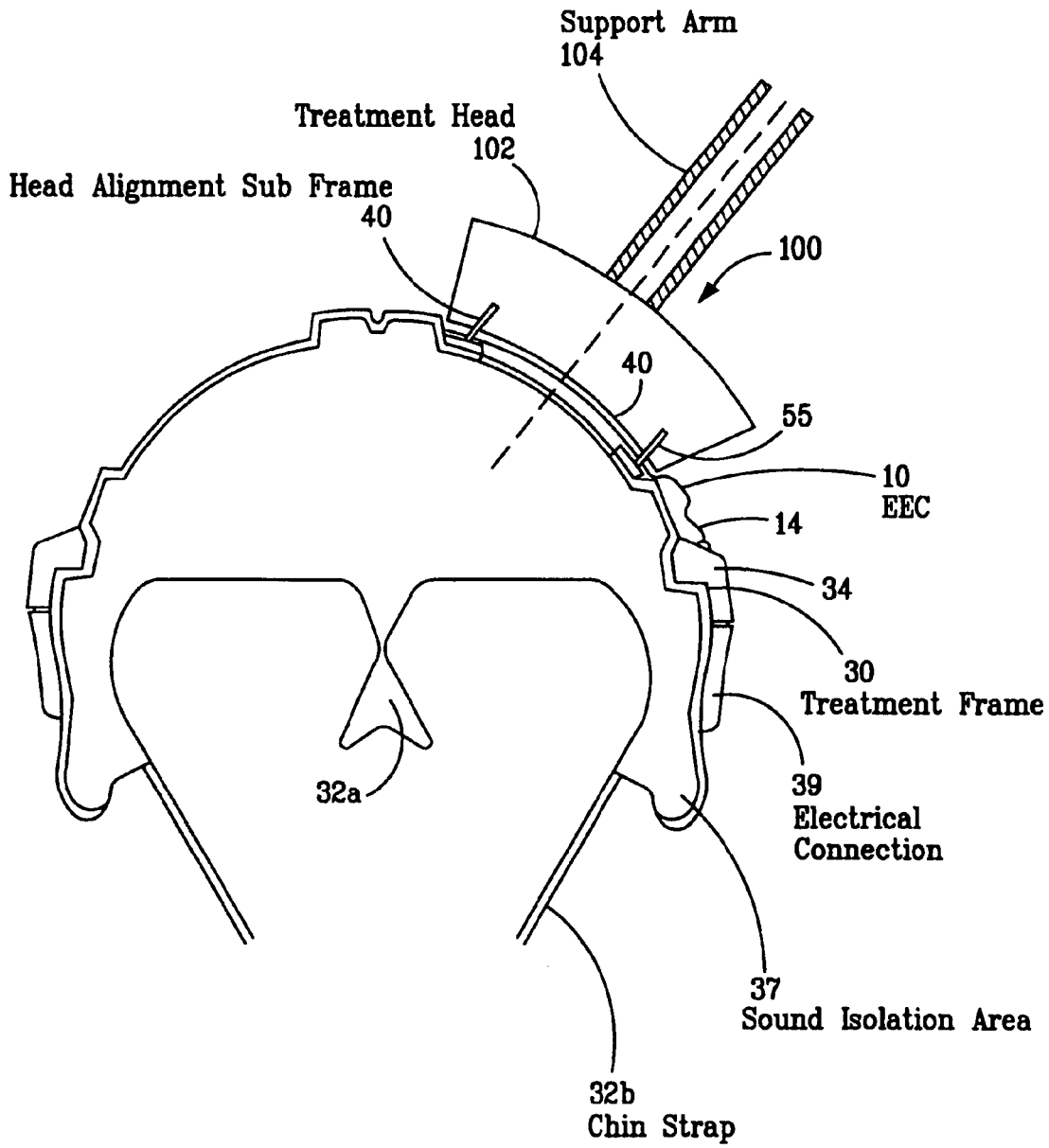
FIG. 2 is a sectional view of the device of FIG. 1 for reducing scalp nerve membrane depolarization in accordance with the invention.

As shown in FIGS. 1 and 2, a flexible circuit or wafer 10 may be made of a polymer or plastic substrate 12 with copper runs imbedded therein. The copper runs may extend out into lead 14 which allows wafer circuit 10 to communicate electrical signals from an external source, like a computer device, for example. Substrate 12 may include an alignment projection 16 for insuring that the wafer circuit is properly oriented. A magnetic field sensor and/or other sensors may be provided within the substrate to measure the magnetic field being provided to the patient (e.g., for calibration or fault detection) and/or take biological readings of the patient. Substrate 12 may further include attachment holes 15 for securing wafer circuit 10 to a specific location with respect to the treatment head and the patient's body.

Wafer circuit 10 may be a single-use and disposable item and is placed over the skin of the patient with a small quantity of conducting gel. Each wafer circuit 10 may be provided with its own small quantity of conducting gel (not shown) and a removable paper or plastic seal (not shown). Upon removal of the paper or plastic seal, the gel may be exposed, and wafer circuit 10 may be affixed to a patient.

As noted above, the invention facilitates the placement of the wafer circuit and the magnetic stimulator device in precisely the proper location on the patient in a repeatable fashion. As such, an inventive locator system 5 includes a treatment frame 30 that may be worn securely on the patient. In the example embodiment shown, frame 30 may be worn on the patient's head for rTMS therapy. Ear protectors 37 may be provided on opposite sides of treatment frame 30 to muffle the sound generated by the rTMS device 100 and/or the dampen vibration caused by the rTMS device 100. The patient's ears are placed inside the hollow ear protectors 37. Frame 30 may include a treatment window 31 onto which wafer circuit 10 may be disposed. Surrounding window 31 may be a series of attachment holes 35 for receiving attachment pegs 55. These pegs 55 may extend above and below the sub-frame 40 and may be passed through attachment holes 15 of wafer circuit 10 to enable the secure attachment of wafer circuit 10 to treatment frame 30. In addition, a series of attachment holes 35 may be provided around window 31 so that wafer circuit 10 may be secured in any of a number of different locations with respect to the frame 30. Attachment holes 35 may be provided in a recess 33. Window 31 may include cutout 36 for accommodating projection 16 of wafer circuit 10.

Treatment frame 30 may further include a securing means 32 for insuring that the frame is placed in the substantially the same manner and substantially the same location on the patient's head. Securing means 32 may include a nose bridge section 32A, a chin strap 32B, and a rear strap 32C. Straps 32B and 32C may be provided with conventional size adjusting structure, e.g., a buckle, frictional fasteners such as VELCRO,-elastic, etc. The straps may each be a single piece of material or be two pieces each attached at opposite sides of the treatment frame which are tied or otherwise fastened together.

Treatment frame 30 may be reusable from patient to patient, or it may be made in a single patient embodiment. For example, a malleable substance may be provided within the main body of frame 30 to enable the healthcare provider to mold the frame to the specific contours of the patient's head more permanently. As a further means of securing the frame to the patient, a portion or all of the frame may be provided with a curable resin that is malleable but will harden when exposed to a certain condition, e.g., a specific wavelength of light, heat, ultrasonics, and the like. A particularly ideal portion of treatment frame 30 to be provided with such curable resin is the nose bridge section 32A, because the nose and bridge section of a person's face is considered very topologically distinctive and easily molded prior to curing the resin.

An additional component, the alignment sub-frame 40, may be provided. Sub-frame 40 is substantially the same shape (but may be smaller in at least one direction) as treatment window 31 and fits within recess 33. Sub-frame 40 is preferably provided with holes 45 for pegs 55. In this embodiment, wafer circuit 10 may be secured to sub-frame 45 and sub-frame 45 may be positioned on treatment frame 30 via pegs 55. The provision of sub-frame 45 is particularly advantageous for the two-step process of dosing and treating an rTMS patient. That is, wafer circuit 30 is first applied to the patient's skull over his motor center to determine the minimum amount of current required to affect his neurons. The motor center is chosen as a preferred dose indicator since the results are extremely easy to spot (i.e., a portion of the body will move). Once the proper dose is determined, wafer circuit 10 may be moved to the treatment location to affect the neurons involved in the patient's depression. By providing system 5 with sub-frame 40, it is easier to move the wafer circuit from one location to the other without disturbing the main treatment frame. An additional support device may be used to aid in maintaining alignment during a therapeutic session.

In operation, treatment frame 30 is secured to the patient's head, and wafer circuit 10 is secured to frame 30 (either with or without sub-frame 40). Support arm 104 (carrying the electrical and any other conduits) of rTMS device 100 is moved so as to position treatment head 102 directly over treatment window 31. When an electric signal is supplied to wafer circuit 10 via lead 14 inserted into outlet 34 of connection 39 (having an electrical lead back to the power supply), circuit 10 may produce an electric field. Wafer circuit 10 is supplied an electrical signal from a waveform generator that is gated by the signal that gates the discharge of the storage capacitor in the rTMS device 100 for the creation of the pulsed magnetic field (from the coil) that induces the undesirable electric fields in the scalp. In this way, the fields (from the rTMS and from wafer circuit 10) are present in the scalp at the substantially the same time. The amplitude of the signal supplied to the wafer circuit may be made to track the amplitude of the signal supplied to the coil such that the electric field produced by wafer circuit 10 is matched yet substantially opposite in polarity to that of the coil.

Wafer circuit 10 makes electrical contact with the scalp through the use of a conducting gel type material. The material in the path of the magnetic field may made to not substantially distort or reduce the induced electric fields produced by the rTMS device in the cerebral cortex of the patient.

The invention is not limited to the above description. Modifications that would be readily apparent to one skilled in the art are contemplated as being within the scope of the invention. For example, although the invention is described as particularly useful for rTMS for the treatment of depression, it is also useful in treatment of epilepsy, specifically temporal lobe epilepsy, because the jaw muscles would be stimulated very uncomfortably during treatment. Other possible conditions that may be treated include the following: epilepsy, schizophrenia, Parkinson's Disease, Tourette's Syndrome, Amyotrophic lateral sclerosis (ALS), Multiple sclerosis (MS), Alzheimer's Disease, Attention Deficit/Hyperactivity Disorder, Obesity, Bipolar disorder/mania, Anxiety disorders (Panic Disorder w and w/o agoraphobia, Social Phobia AKA Social Anxiety Disorder, Acute Stress Disorder, Generalized Anxiety Disorder), Post-traumatic stress disorder (one of the Anxiety Disorders in DSM), Obsessive compulsive disorder (one of the Anxiety Disorders in DSM), Pain (migraine, trigeminal neuralgia, Chronic pain disorders including neuropathic pain (e.g., pain due to diabetic neuropathy, post-herpetic neuralgia), idiopathic pain disorders (e.g., fibromyalgia, regional myofascial pain syndromes), Rehabilitation following stroke (neuro plasticity induction), Tinnitus, Stimulation of implanted neurons to facilitate integration, Substance-related disorders (dependence and abuse and withdrawal diagnoses for alcohol, cocaine, amphetamine, caffeine, nicotine, cannabis), Spinal cord injury & regeneration/rehabilitation, Head injury, Sleep deprivation reversal (DARPA), Primary sleep disorders (Primary insomnia, primary hypersomnia, circadian rhythm sleep disorder), Cognitive enhancements, Dementias, Premenstrual dysphoric disorder (PMS), Drug delivery systems (changing the cell membrane permeability to a drug), Induction of protein synthesis (induction of transcription and translation), Stuttering, Aphasia, Dysphagia, Essential tremor, and Eating Disorders (Bulimia, Anorexia, Binge Eating).

Indeed, a frame of the type disclosed above for the patient's head is equally adaptable for other parts of the body, with geometric changes to account for the varying topography of the human body. Also, the invention is described as applying a current or e-field of substantially equal strength to that of the induced current to cancel the e-field in the skin. It is also contemplated that an applied current of less than the induced current (or more than the induced current, if convenient to do so) so as to merely reduce the e-field in the skin and thus reduce the discomfort. The invention is also contemplated to be useful with other monitoring, therapeutic, or imaging devices such as an EEG.

What is claimed is:

1. A device for placing a treatment component on a patient's head, comprising:
   an attachment frame that attaches the treatment component to the patient's head, wherein the attachment frame comprises a window;
   a receiving mechanism that holds the treatment component to the attachment frame;
   an alignment structure that permits the treatment component to be positioned at a desired location on the patient's head; and
   an adjustment structure that is capable of adjusting the device to the contours of an individual patient's head.

2. The device of claim 1, wherein the alignment structure comprises at least one hole that permits the patient's head to be marked.

3. The device of claim 1, further comprising an isolator component.

4. The device of claim 3, wherein the isolator component is capable of accomplishing at least one of the following: reducing sound to the patient's ears and reducing vibration of the attachment frame.

5. The device of claim 1, further comprising an electrical connector to send and receive data as a function of the treatment.

6. The device of claim 1, wherein the adjustment structure comprises a malleable material to mold to the patient's head.

7. The device of claim 6, wherein the malleable material hardens as a function of at least one of the following: a predetermined wavelength of light, heat, and an ultrasonic signal.

8. The device of claim 1, wherein the alignment structure permits the treatment component to be placed in substantially the same location for each patient treatment.

9. The device of claim 1, wherein at least a portion of the adjustment structure spans the patient's nose.

10. The device of claim 1, wherein the window includes at least one hole that permits attachment to a flexible circuit.

11. The device of claim 1, further comprising a securing structure that includes at least one of the following: a nose bridge component, a chin strap component, and a rear strap component.

12. The device of claim 1, wherein the attachment frame is reusable.

13. The device of claim 1, wherein the attachment frame is rendered unusable.

14. The device of claim 13, wherein the attachment frame automatically is rendered unusable at the conclusion of each patient treatment as a function of modification of at least one of the following: the attachment frame, the electrical connector, the alignment structure, receiving mechanism, and the malleable material.

15. The device of claim 1, wherein the treatment component is a magnetic stimulation device used for transcutaneous magnetic stimulation treatment of the patient.

16. The device of claim 15, wherein the magnetic stimulation device comprises an arc-shaped core spanning an angle of less than three hundred sixty degrees, and wherein the core comprises a highly saturable magnetic material having a magnetic saturation of at least 0.5 Tesla.

17. A system for placing a treatment device on a patient, comprising:
   a treatment component;
   a head-frame component for placing a treatment component on a patient's head, comprising:
      an attachment frame that attaches the treatment component to the patient's head, wherein the attachment frame comprises a window,
      a receiving mechanism that holds the treatment component to the attachment frame, and
      an alignment structure that permits the treatment component to be positioned at a desired location on the patient's head,
      an adjustment structure that is capable of adjusting the device to the contours of an individual patient's head;
   a flexible circuit capable of being attached to the head-frame component; and
   an electrical connector that communicates data as a function of the treatment component, wherein the electrical connector is in communication with the flexible circuit.

18. The system of claim 17, wherein the flexible circuit comprises a magnetic field sensor to measure the magnetic field being provided to the patient.

19. The system of claim 17, wherein the data communicated comprises at least one of the following: calibration information, detection of fault or operation of the treatment device, the patient's biological measurements.

20. The system of claim 17, wherein the treatment component is a magnetic stimulation device used for transcutaneous magnetic stimulation treatment of the patient.

21. The system of claim 20, wherein the magnetic stimulation device comprises an arc-shaped core spanning an angle of less than three hundred sixty degrees, and wherein the core comprises a highly saturable magnetic material having a magnetic saturation of at least 0.5 Tesla.

22. A method of placing a treatment device on a patient, comprising:
   placing a head-frame component on the patient's head;
   aligning the head-frame component to the patient's head;
   securing the head-frame component to the patient;
   attaching a treatment device to the head-frame component; and
   adjusting the device to the contours of an individual patient's head.

23. The method of claim 22, further comprising connecting the head-frame component to a computing device.

24. The method of claim 22, further comprising causing a malleable portion of the adjustment structure to mold to the patient's head by providing at least one of the following: a predetermined wavelength of light, heat, and an ultrasonic signal.

25. The method of claim 22, further comprising placing the head-frame component in substantially the same location as a previous patient treatment.

26. The method of claim 22, further comprising rendering the head-frame component unusable.

* * * * *